(12) United States Patent
von Arx et al.

(10) Patent No.: US 9,411,027 B2
(45) Date of Patent: Aug. 9, 2016

(54) METHOD FOR DETERMINING IF AN IMPLANTABLE MEDICAL DEVICE IS MAGNETIC RESONANCE CONDITIONAL

(71) Applicant: BIOTRONIK SE & Co. KG, Berlin (DE)

(72) Inventors: Jeffrey A. von Arx, Lake Oswego, OR (US); Volker Lang, Berlin (DE)

(73) Assignee: BIOTRONIK SE & Co. KG, Berlin (DE)

( * ) Notice: Subject to any disclaimer, the term of this patent is extended or adjusted under 35 U.S.C. 154(b) by 224 days.

(21) Appl. No.: 14/038,205

(22) Filed: Sep. 26, 2013

(65) Prior Publication Data

US 2014/0163892 A1 Jun. 12, 2014

Related U.S. Application Data

(60) Provisional application No. 61/735,073, filed on Dec. 10, 2012.

(51) Int. Cl.
*G01N 33/48* (2006.01)
*G01R 33/28* (2006.01)
*G06G 7/58* (2006.01)
*G06F 19/00* (2011.01)

(52) U.S. Cl.
CPC .......... *G01R 33/288* (2013.01); *G06F 19/3406* (2013.01); *G06F 19/322* (2013.01)

(58) Field of Classification Search
CPC ........................... G06F 19/3406; G06F 19/322
See application file for complete search history.

(56) References Cited

U.S. PATENT DOCUMENTS 7,676,272 B2 * 3/2010 Lang .................... A61N 1/3708
128/905

* cited by examiner

*Primary Examiner* — Eric S DeJong
(74) *Attorney, Agent, or Firm* — Arc IP Law, PC; Joseph J. Mayo

(57) ABSTRACT

A method for determining if an implantable medical device (IMD) in a patient is magnetic resonance conditional. Embodiments include a Home Monitoring Service Center (HMSC) that indicates if the IMD is MR conditional and what those conditions are. The IMD includes memory with flags, enabling a physician to set a flag to "MR conditional" if the IMD is MR conditional, if there are no abandoned leads in the patient, and if there are no other hardware in the patient that are not MR conditionally approved. In embodiments, the flags indicate safe for 1.5 T, 3.0 T, 1.5 & 3.0 T, up to 2 W/Kg, up to 4 W/Kg, with/without exclusion zone, and date flags are set. During home monitoring, the HMSC reads out a status of the MR conditional flags and the date last confirmed. If the patient needs an MRI scan, physician queries HMSC to determine MR conditional status.

20 Claims, 3 Drawing Sheets

METHOD FOR DETERMINING IF AN IMPLANTABLE MEDICAL DEVICE IS MAGNETIC RESONANCE CONDITIONAL

This application claims the benefit of U.S. Provisional Patent Application 61/735,073, filed on 10 Dec. 2012, the specification of which is hereby incorporated herein by reference.

BACKGROUND OF THE INVENTION

1. Field of the Invention

At least one embodiment of the invention generally relates to medical device safety method and more particularly, but not by way of limitation, relates to a method for determining if an implantable medical device is magnetic resonance conditional and hence poses no hazards with respect to a specified magnetic resonance imaging environment with specified conditions of use.

2. Description of the Related Art

Traditional methods for determining if an implanted medical system is "Magnetic Resonance (MR) conditional" are time consuming, costly and in many cases involve unbillable tasks. For example, recognized solutions require multiple physicians to potentially determine information that should be known at implant time. Furthermore, recognized solutions do not ensure that conservative settings are enforced in cases where programming is not completed at implant time. In addition, typical solutions fail to periodically update external databases with status, e.g., nightly during home monitoring uploads, and thus may not reflect the current status of the implanted system.

An MR conditional system, for example, is a system that has been demonstrated to pose no known hazards in a specified Magnetic Resonance Imaging (MRI) environment with specified conditions of use. Example conditions that define the MRI environment include static magnetic field or specific absorption rate (SAR) for example. In order for a system to be MR conditionally safe, both the implanted medical device and associated leads need to be MR conditional, without any non-MR conditional abandoned leads or other non-MR conditional hardware implanted in the patient. Furthermore, the MR conditions for which a system is approved for vary, and are a function of both the specific implantable device and implanted leads.

An "MR Safe" system, for example, is a system that poses no known hazards in all MR environments. Example MR Safe materials include non-conducting, non-metallic and non-magnetic materials such as plastic.

An "MR Unsafe" system, for example, is a system known to pose hazards in all MRI environments. Example MR unsafe materials include some conductive electrode leads and ferromagnetic materials. Due to the extreme strength of magnetic fields used for MRIs, ferromagnetic materials are generally considered dangerous in the MR environment and have been known to cause the so called "missile-effect", where ferromagnetic materials are accelerated in the magnetic field to dangerous kinetic energies.

Before a radiologist performs an MRI on a patient having a cardiac rhythm management (CRM) device or other implantable medical device or system, the radiologist must determine if the implanted system is MR conditionally safe. Since there is no known easy manner for determining if the implanted system is MR conditionally safe, the radiologist either does not give the patient the MRI, or alternatively, calls the implanting cardiologist to ask whether the system is MR conditional.

If no MRI occurs, the patient may be denied a procedure that is beneficial, life extending or life saving, simply because the radiologist does not have information that should be known a priori regarding the implanted system.

Alternatively, the radiologist may call the cardiologist who looks through the patient files, and generally receives no reimbursement for this task. However, a phone call to the implanting physician or cardiologist has disadvantages. The implanting physician generally does not want to be bothered with phone calls every time a patient needs to be cleared for an MRI. Phone calls tend to take up the time of the implanting physician's staff, and are generally not billable.

In this scenario, the implanting cardiologist may read the patient's file and may write a memo to the radiologist indicating whether the system is MR conditional or not. If the records cannot be found, for example if the patient has changed cardiologists, then the cardiologist will order a chest X-ray to look for X-ray markers, devices and abandoned leads and, in combination with device interrogation, the cardiologist may attempt to determine if the implanted system is an MR conditional safe system. This occurs even though the data regarding the implanted system should be known a priori. However, X-rays have well known risks, added costs, and tend to complicate the MRI workflow. Furthermore, different X-ray markers are required to indicate if a system is conditionally safe for 1.5 T, 3.0 T, both 1.5 T & 3.0 T, up to 2 W/Kg, up to 4 W/Kg, with exclusion zone, without exclusion zone, etc. It is difficult to make so many distinctions in small X-ray markers, which limits their usefulness.

In summary, there is no consistent manner in which to identify if an implanted system is MR conditional, and what the conditions are. Therefore, some patients who have MR conditional systems are denied MRI scans because of the difficulty in verifying that their implanted systems are MR conditional, and many patients are denied MRIs today who would benefit from them. Hence, there is a need for a method for determining if an implantable medical device is magnetic resonance conditionally safe.

BRIEF SUMMARY OF THE INVENTION

Embodiments of the system may generally be programmed at time of implantation, or at a later time, with information indicating if the system is MR conditional and what those conditions are. At the time of implantation, or later, the implanter or other physician may possess all MR conditional data related to the implanted hardware and the absence, or presence, of abandoned leads. Therefore, if done at time of implantation no extra X-rays and only minimal effort is required to specify the MR conditional status of the system at implantation time. At each follow-up, the physician may be queried, by the programmer, about the status of the implanted system. Since the status of an MR conditional system can change if a new lead is implanted, breaks or is unused, the system may keep the information up to date through the query. In one or more embodiments, the information is not only stored in the implant, but may be uploaded to an associated patient device and/or the Home Monitoring Service Center (HMSC), or other central data management center daily, such that the HMSC may retain the MR conditional status of the implanted system, as well as the time and/or date that the MR conditional status was last confirmed in a follow-up. A radiologist or other person that is to perform an MRI may then query the HMSC and obtain this information in a rapid fashion, which may ensure that a life saving MRI is conducted in some time sensitive scenarios.

The implantable device may contain memory locations for flags which may be implemented as memory values at memory locations, which indicate if an implanted system is MR conditional or not, if not why not, and if so, what the MR conditions are. For example, one flag may be utilized to indicate if the system is MR conditional or not, while another flag may indicate the presence of abandoned leads. Another flag may indicate the presence of leads that are not MR conditional. Another flag may indicate if the system is MR conditional with, or without an exclusion zone. Another flag may indicate if the system is MR conditional up to 2 W/kg, i.e., normal mode. Another flag may indicate if the system is MR conditional up to 4 W/kg, i.e., first level control mode. Another flag may indicate if the system is MR conditional for 1.5 T scanners, while another flag may indicate if the system is MR conditional for 3 T scanners.

In one or more embodiments, the flags may default to the most conservative settings. In this manner, if they are not programmed, the interpretation is the most conservative setting. For example, the flag indicating if the system is MR conditional may default to "not MR conditional". Hence, if the flags are not programmed at all, the assumption is the most conservative one, or lowest MR conditional value that the system is not MR conditional. If the MR conditionally safe flag is set, the other flags may default to the most conservative settings, i.e. up to 2 W/kg, with exclusion zone only. Thus, for example, if an implanter is distracted and only sets a subset of the flags before sending the patient home, the settings of the remaining flags may be set to the most conservative.

In one or more embodiments of the method, these flags may be implemented with interlocks to ensure safe programming, and to ensure that programming is not contradictory. For example, in one embodiment, the system may accept information that indicates that the system is MR conditional, and if the information is not consistent with the configuration of the implantable devices, e.g., IMDs and/or leads, then the flag indicating the presence of an abandoned lead cannot be set. If an attempt to set a contradictory condition is received by the system, a warning may be displayed by the system on the programmer screen, for example indicating that the system must be set to non-MR conditional when an abandoned lead is present.

The date, and optionally time, that the flags are programmed, or re-programmed, may automatically be recorded in the implanted device in one or more embodiments. This enables anyone reading the MR conditional status of the system to be able to read out when the MR conditional status was last programmed or otherwise updated. In addition, at subsequent follow-ups, the person performing the follow-up may be prompted by the programmer to confirm that the MR conditional status is still applicable, e.g., that no lead replacement has occurred since the last follow-up. The date and optional time of the most recent confirmation may also be recorded in at least one of the implanted medical devices in one or more embodiments, i.e., recorded in memory of the IMD of a system that includes electrode leads for example. This allows anyone reading the MR conditional status of the system to know when the status was last confirmed.

In one or more embodiments, every day during the daily home monitoring upload, the status of all the MRI conditional flags, as well as the dates that the flags were last set and the dates the status was last confirmed, may be uploaded to the HMSC. This information may be stored on the HMSC servers. When a request comes into the HMSC from a radiologist or other personnel with patient consent, for example via a scanned patient consent form, then HMSC personnel may check the servers for the MR conditional status of that particular patient, and the date it was last confirmed and release this information to the requestor. This enables the physician to schedule an MRI without directly querying the information in the implanted device, or to confirm the information stored in the implantable medical device for example.

In one or more embodiments, a physician that does not have enough time during implantation does not need to program the MR conditional status, but may change MR conditional status via HMSC remote programming after implantation, or during an aftercare visit of the patient, using a programmer or other external device.

Advantages of the system are many. For example, the system may reduce workload for the implanter. In addition, for example, the implanter does not receive phone calls from radiologist asking about the MR conditional status of a particular patient. This is of great benefit, because implanters may preferentially choose embodiments of the system over other devices due to the reduced overhead of managing MR conditional status requests. Embodiments of the system may reduce work for the radiologist as well. The radiologist of a patient utilizing an embodiment of the system may call a single phone number, or query a website, or in any other manner query the HMSC to determine the MR conditional status of the device, without the need for the patient to be at the location of the radiologist and without directly querying the patient's implanted device. For example, the radiologist does not need to refer the patient back to the implanter for a consultation. In addition, embodiments of the system may reduce the risk of a patient being denied a medically necessary MRI scan. This risk is reduced since it is easy for the radiologist to query the HMSC service center, generally 24-hours a day, to find out if the implanted system is MR conditional and what the conditions are. Furthermore, the system may reduce the risk of a patient being given an extra exploratory chest X-ray to check for abandoned leads prior to an MRI and also reduces the risk of a patient getting an aggressive MRI scan which violates the conditions under which the system has been shown to be safe. Embodiments of the method enable these advantages by making the MR conditional status readily available to the radiologist, even if the patient is unconscious, for example by querying the implantable medical device for a serial number or other identification that may be utilized at the HMSC to identify the patient and obtain the MR conditional status.

BRIEF DESCRIPTION OF THE DRAWINGS

The above and other aspects, features and advantages of at least one embodiment of the invention will be more apparent from the following more particular description thereof, presented in conjunction with the following drawings wherein.

DETAILED DESCRIPTION OF THE INVENTION

The following description is of the best mode presently contemplated for carrying out at least one embodiment of the invention. This description is not to be taken in a limiting sense, but is made merely for the purpose of describing the general principles of the invention. The scope of the invention should be determined with reference to the claims.

Figure 1:
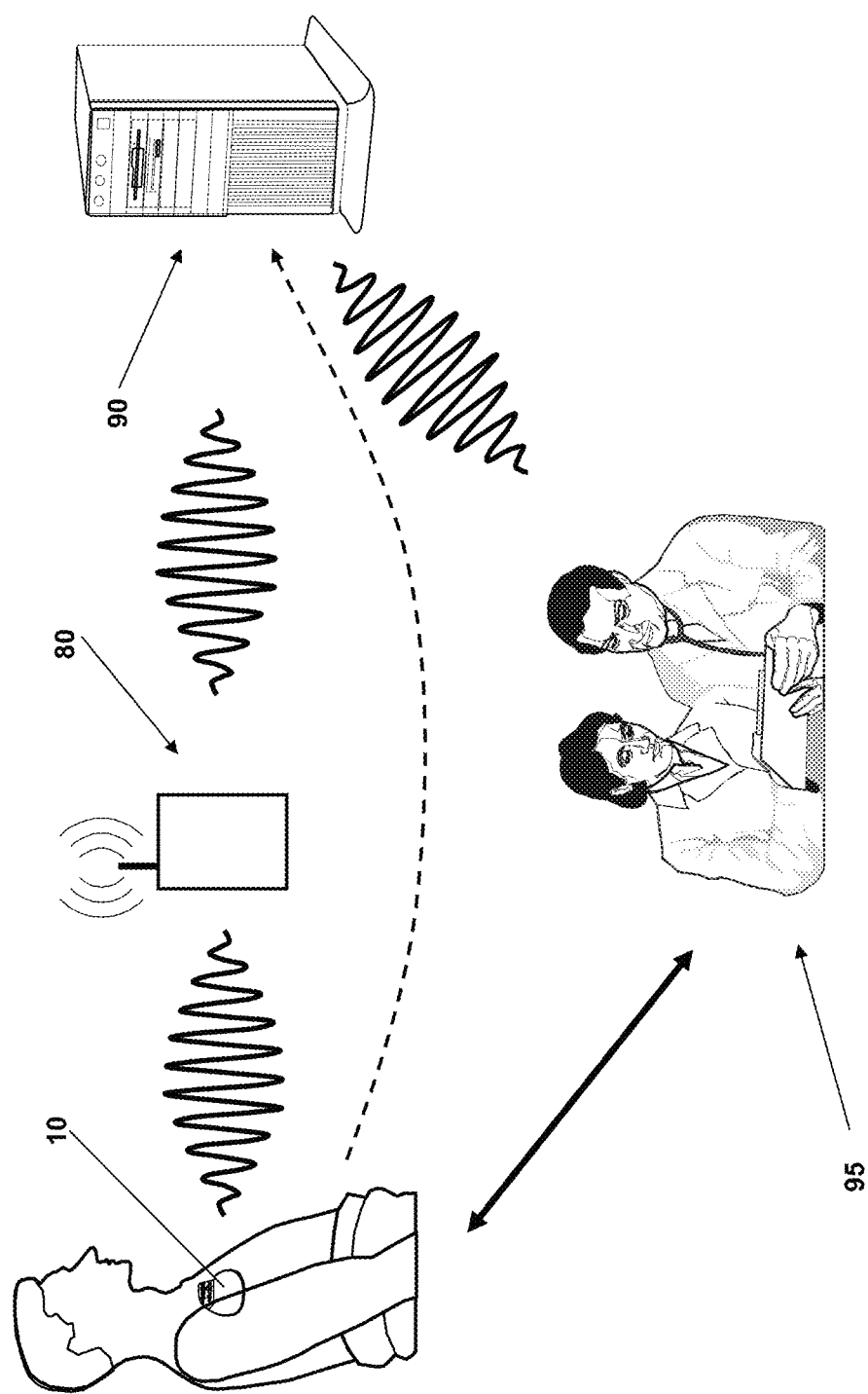
FIG. 1 shows a system view of an embodiment of the invention.

FIG. 1 shows an implantable device system including implantable medical device 10 that may be implanted within a patient, external device 80 and home monitoring service center (HMSC) 90 communicatively coupled with one another, for example coupled wirelessly. Implantable medical device 10 is, for example, an implantable pacemaker, an implantable cardioverter/defibrillator, device for cardiac resynchronization, or electrode leads connected thereto, or any combination thereof. Implantable medical device 10 generally includes an implant transceiver that allows for wireless communication with the external device. The external device may be implemented as an external patient device and/or programmer for example. External device 80 generally includes an external transceiver unit that allows for wireless communication with the implant transceiver and a data communication interface that enables data communication with home monitoring service center 90. The data communication interface may use a public data communication line such as a telephone landline connection or wireless connection via GPRS/UMTS or SMS, or any other communication interface that is capable of transmitting data to the HMSC 90. In one or more embodiments, the system may include two external devices, i.e., an external patient device that is separate from the programmer device as one skilled in the art will appreciate, but which is not shown for brevity.

HMSC 90 may include or may be connected to a user interface allowing a physician or a team of physicians 95, such as an implanting physician and/or radiologist as shown, to interact with the HMSC 90. The user interface may display data to the physicians 95 and may provide an input device allowing the physicians 95 to enter instructions or data into HMSC 90.

HMSC 90 further generally includes a central database that may be connected to the data communication interface and any optional data evaluation module that may be connected to the database that is configured to evaluate data stored on said database.

A patient having implanted medical device 10 may communicate with the implantable medical device 10, HMSC 90 or both, by means of the external device 80. For this purpose, the external device 80 may feature a user interface or may be automated to act as a gateway to HMSC 90 that does not require any user input. The patient may also directly connect with HMSC 90 without using the external patient device but rather via the Internet, or in any other manner for example. Physicians 95 may communicate with implanted medical device 10 via the external device, for example via a programmer.

Any type of implantable medical device 10 may be categorized by embodiments of the system, including pacemakers and cardioverters/defibrillators that may be connected to pacing/sensing leads placed in a heart of the patient or in any other portion of the body of the patient, for example.

Figure 2:
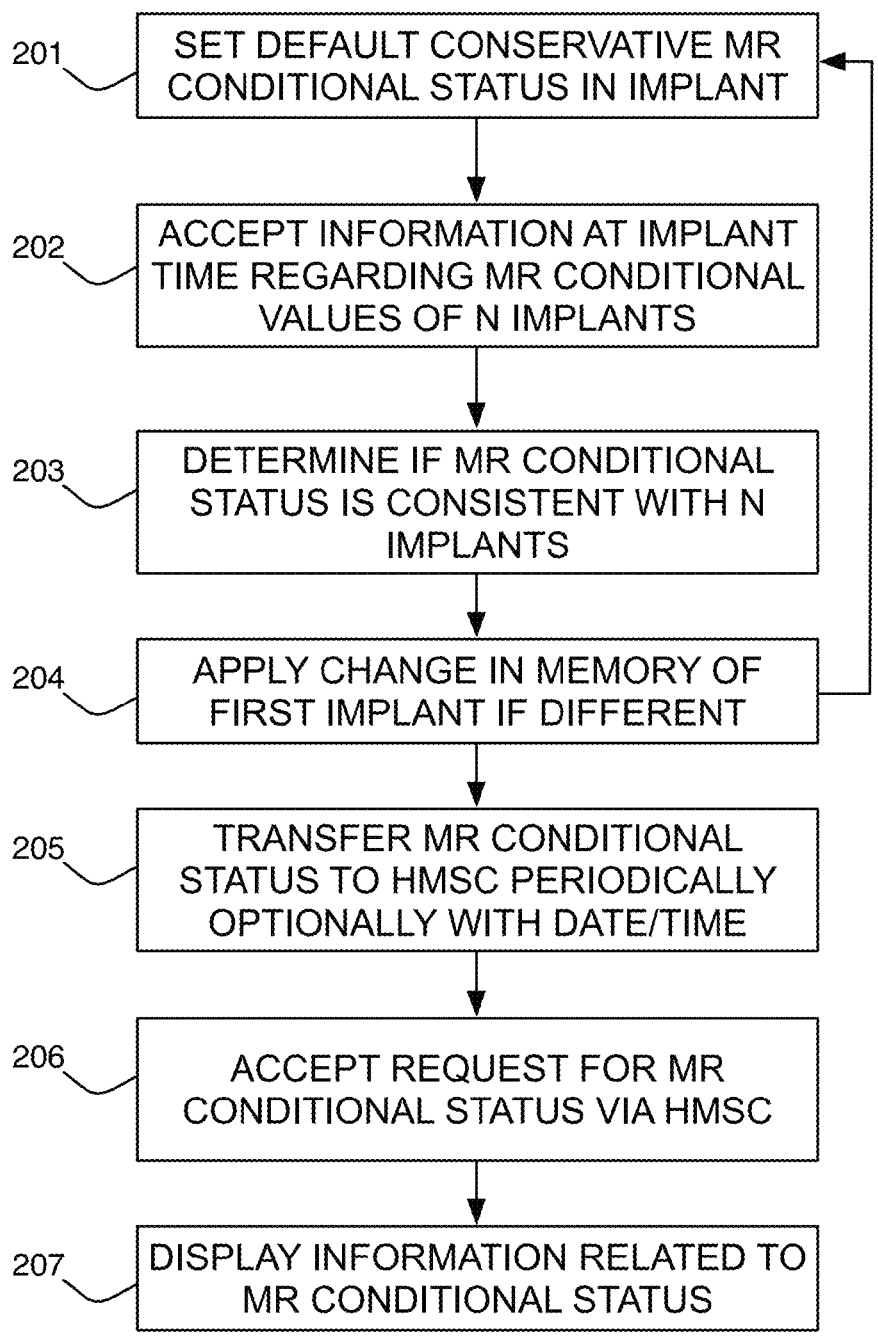
FIG. 2 shows a flow chart of an embodiment of the method.

FIG. 2 shows a flow chart of an embodiment of the method for determining if an implantable medical device is magnetic resonance conditional. Embodiments generally set a default conservative magnetic resonance condition status in a memory of a first implantable medical device implanted in a patient at 201. In one or more embodiments, this may involve ensuring that if programming is interrupted, as shown at step 204 below for example, that the implant has a minimally acceptable MR conditional status to enable at least a minimally aggressive MRI to occur. One or more embodiments may also set a date and time of examination in the implant at the start of the examination so that the date/time of the MR conditional status may be checked, e.g., at 206 to determine if the information was fully updated at the examination or is waiting for the physician to update the information to determine whether to proceed with an MRI or not. As the implant or other procedure occurs, or later when a physician has time to enter information, the information related to N implants, i.e., IMDs, electrodes, broken or unused electrodes, etc., may be accepted by the system, for example via an external device such as an external programmer at 202.

Embodiments of the method may determine if the information related to magnetic resonance conditional status is consistent with status of the at least one implantable medical device implanted in the patient at 203. For example, if information related to an unused electrode lead is entered into the external device at 202, then if the MR conditional status is already at a level of MR conditional at certain Watts/Kg with exclusion zone based on the implants with information already entered, then the current MR conditional status is determined to be "not MR conditional" at 203 based on the potentially hazardous unused lead. Since the current status may not be consistent with the information just accepted by the external device, a new MR conditional status may be determined. The MR conditional status may be set to the lowest MR conditional value associated with a plurality of implantable medical devices for example. Embodiments of the method, for example, may apply a change in status in the memory of the first implantable device, if the information related to magnetic resonance condition status is different than the status of the at least one implantable medical device at 204. Hence, the MR conditional status may change as more information is accepted by the external device that is up to date with the current configuration of implanted elements within the patient. The status may increase or decrease, allow more or less aggressive MRIs respectively, as leads are connected or replaced, or as broken leads are discovered, etc. The date or time or date and time may also be stored in the memory of the first implant at this time, so that a determination of the validity of the data may be made before performing an MRI or for any other reason. Applying the change may include setting an MR conditional flag in memory to "not MR conditional" or "MR conditional", setting MR conditional exclusion or non-exclusion values, setting an MR conditional value that is indicative of abandoned leads and non-MR conditional leads, and setting an MR conditional value that may be indicative of MR watts per kilogram flag, normal mode, first level control mode, and MR scanner power value, or any combination thereof. Processing continues at 201 until all implants are described or programming is otherwise completed, for example if an implanting physician does not have enough time to specify all implant information.

Embodiments of the method may transfer the MR conditional status related to magnetic resonance condition status to a home monitoring service center periodically at 205, for example along with information transferred daily, or in any reoccurring period, e.g., during home monitoring data upload. Embodiments of the method may accept a request for the information related to magnetic resonance conditional status of the at least one implantable medical device at the home monitoring service center at 206. Since the HMSC is generally available 24 hours a day, the doctor that desires to perform an MRI examination of a patient does not have to call another physician, wait for information from staff members, or otherwise delay the MRI, as the information is displayed at 207, enabling rapid access to at least minimally MRI aggressive values, that are generally updated daily via the home monitoring data upload. Other embodiments of the method at 206 may also obtain a serial number associated with the first implantable medical device, transfer the serial number to the home monitoring service center and obtain the identity of the patient based on the serial number and display that information at 207.

Figure 3:
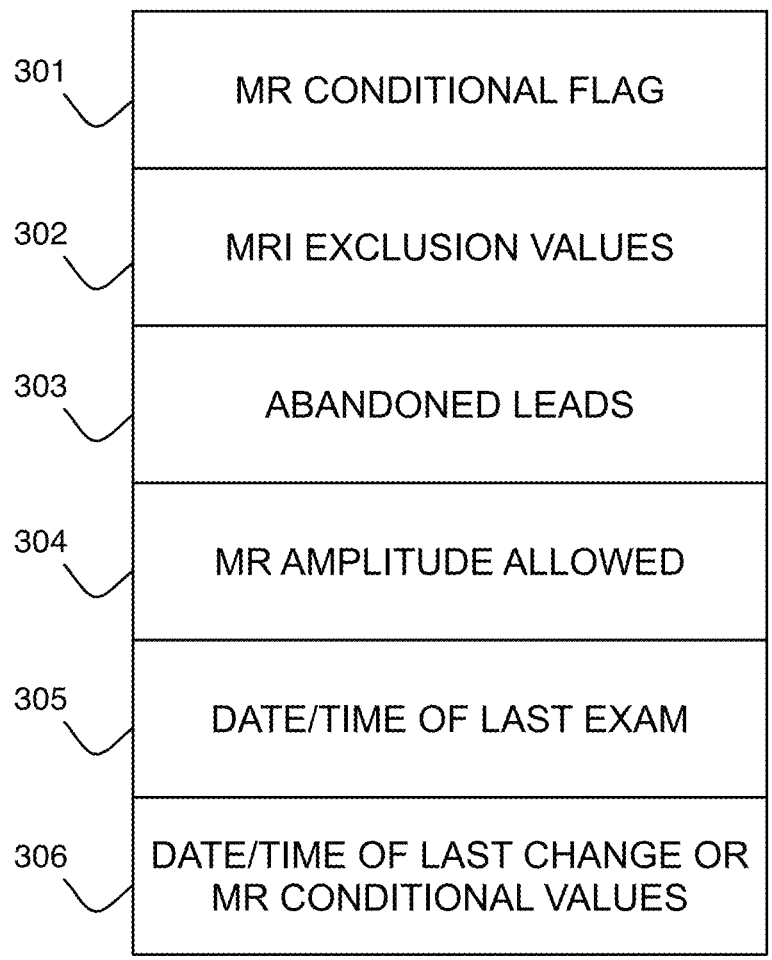
FIG. 3 shows a memory structure that enables an embodiment of the invention.

FIG. 3 shows a memory structure that enables an embodiment of the invention. Memory location 301 may be implemented as a Boolean value or any size memory structure that stores information related to MR conditional or not MR conditional. Memory location 302 may include information related to whether the system is MR conditional with or without exclusion zones and information related to any exclusion zones, for example. The information concerning the exclusion zones may be presented by exclusion values. Memory location 303 may include information related to abandoned leads including number or type or any information related to the functionality of the leads, whether broken or not and whether MR conditional or not, i.e., some unused leads may include passive components that detune the leads, which may still allow a system with unused leads to be MR conditional for example. Memory location 304 may include information related to the maximum MRI power, for example up to 2 W/kg, which is typically as normal mode, up to 4 W/kg, which is typically as first level, etc. Memory location 304 may be implemented as separate flags, or bits, or may be implemented with a size that enables entry of multiple values associated with each amplitude allowed. In addition, memory location may store information related to whether the system is MR conditional for 1.5 T scanners, or for 3 T scanners or any other value. Alternatively or in addition to, memory location 304 may be implemented with multiple flags or memory locations. Memory location 305 may optionally include the date and/or time of the last examination. Memory location 306 may include the date/time of the last change in MR conditional values, so that a sanity check on the last examination, as optionally stored in memory location 305, may be conducted to determine if the examination was started but did not complete when the values were changed, indicating that the MRI should be carefully conducted, for example after consultation with the implanting physician. Alternatively or in addition to, if the information is up to date, then the MRI may be conducted with the values at hand, for example as per the memory of the implant or values retrieved from the HMSC or both in combination if they are in agreement, for example to ensure safety.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

What is claimed is:

1. A method for determining if an implantable medical device is magnetic resonance (MR) conditional comprising:
    setting a default conservative magnetic resonance (MR) condition status in a memory of a first implantable medical device implanted in a patient,
        wherein said implantable medical device comprises an implant transceiver,
        wherein said memory comprises memory locations for flags that correspond to memory values, and
        wherein setting a default conservative MR condition status comprises setting the flags with the default conservative MR condition status;
    accepting information in an external device at an implantation time or a later time related to magnetic resonance (MR) condition status of at least one second implantable medical device implanted in said patient,
        wherein said external device is wirelessly communicatively coupled with said first implantable medical device,
        wherein said external device comprises
            an external transceiver that wirelessly communicates with said implant transceiver,
            a data communication interface, and
            a programmer with a programmer screen; and,
        wherein said information is accepted as entered via said programmer;
    determining if said information related to magnetic resonance (MR) conditional status is consistent with status of said at least one second implantable medical device implanted in said patient via said programmer;
    applying a change in status in said memory of said first implantable device if said information related to magnetic resonance (MR) condition status is consistent with said status of said at least one second implantable medical device via said external device wirelessly communicatively coupled with said first implantable medical device; and,
    transferring said information related to magnetic resonance (MR) condition status to a home monitoring service center periodically via said data communication interface, wherein said home monitoring service center is communicatively coupled with said external device via said data communication interface.

2. The method according to claim 1, wherein said setting said default conservative magnetic resonance condition status comprises setting a status value of not MR conditional.

3. The method according to claim 1, wherein said accepting said information includes accepting information associated with MR conditional values of an electronic implant or an electrode lead or both.

4. The method according to claim 1, wherein said determining if said information related to magnetic resonance conditional status is consistent with status of said at least one second implantable medical device implanted in said patient comprises determining a lowest MR conditional value associated with a plurality of implantable medical devices.

5. The method according to claim 1, wherein said applying said change in status in said memory of said first implantable device comprises storing a date, a time, or a combination thereof in said memory associated with said applying said change.

6. The method according to claim 1, wherein said applying said change in status in said memory of said first implantable device comprises setting an MR conditional flag in said memory to not MR conditional or to MR conditional.

7. The method according to claim 1, wherein said applying said change in status in said memory of said first implantable device comprises setting an MR conditional exclusion or non-exclusion value.

8. The method according to claim 1, wherein said applying said change in status in said memory of said first implantable device comprises setting an MR conditional value that is indicative of abandoned leads and non-MR conditional leads.

9. The method according to claim 1, wherein said applying said change in status in said memory of said first implantable device comprises setting an MR conditional value that is indicative of MR watts per kilogram flag, normal mode, first level control mode, MR scanner power value or any combination thereof.

10. The method according to claim 1, wherein said transferring said information related to magnetic resonance condition status to said home monitoring service center occurs during a home monitoring data upload.

11. The method according to claim 1, further comprising:
accepting a request for said information related to magnetic resonance condition status of said at least one second implantable medical device at said home monitoring service center; and,
displaying said information related to magnetic resonance condition status.

12. The method according to claim 1, further comprising:
obtaining a serial number associated with said first implantable medical device;
transferring said serial number to said home monitoring service center; and,
obtaining an identity of said patient based on said serial number.

13. A method for determining if an implantable medical device is magnetic resonance (MR) conditional comprising:
setting a default conservative magnetic resonance (MR) condition status in a memory of a first implantable medical device implanted in a patient,
wherein said implantable medical device comprises an implant transceiver,
wherein said memory comprises memory locations for flags that correspond to memory values, and
wherein setting a default conservative MR condition status comprises setting the flags with the default conservative MR condition status;
accepting information in an external device at an implantation time related to magnetic resonance (MR) condition status of at least one second implantable medical device implanted in said patient,
wherein said external device is wirelessly communicatively coupled with said first implantable medical device,
wherein said external device comprises
an external transceiver that wirelessly communicates with said implant transceiver,
a data communication interface, and
a programmer with a programmer screen; and,
wherein said information is accepted as entered via said programmer;
determining if said information related to magnetic resonance (MR) conditional status is consistent with status of said at least one second implantable medical device implanted in said patient via said programmer;
applying a change in status in said memory of said first implantable device if said information related to magnetic resonance (MR) condition status is consistent with said status of said at least one second implantable medical device via said external device wirelessly communicatively coupled with said first implantable medical device;
transferring said information related to magnetic resonance (MR) condition status to a home monitoring service center during a home monitoring data upload via said data communication interface, wherein said home monitoring service center is communicatively coupled with said external device via said data communication interface, and wherein said home monitoring service center comprises a user interface;
accepting a request for said information related to magnetic resonance (MR) condition status of said at least one second implantable medical device at said home monitoring service center via said user interface; and,
displaying said information related to magnetic resonance (MR) condition status via said user interface.

14. The method according to claim 13, wherein said setting said default conservative magnetic resonance condition status comprises setting a status value of not MR conditional.

15. The method according to claim 13, wherein said accepting said information includes accepting information associated with MR conditional values of an electronic implant or an electrode lead or both.

16. The method according to claim 13, wherein said determining if said information related to magnetic resonance conditional status is consistent with status of said at least one second implantable medical device implanted in said patient comprises determining a lowest MR conditional value associated with a plurality of implantable medical devices.

17. The method according to claim 13, wherein said applying said change in status in said memory of said first implantable device comprises storing a date, a time or a combination thereof in said memory associated with said applying said change.

18. The method according to claim 13, wherein said applying said change in status in said memory of said first implantable device comprises
setting an MR conditional flag in said memory to not MR conditional or to MR conditional,
setting an MR conditional exclusion or non-exclusion value,
setting an MR conditional value that is indicative of abandoned leads and non-MR conditional leads, and
setting an MR conditional value that is indicative of MR watts per kilogram flag, normal mode, first level control mode, MR scanner power value or any combination thereof.

19. The method according to claim 13, further comprising:
obtaining a serial number associated with said first implantable medical device;
transferring said serial number to said home monitoring service center; and,
obtaining an identity of said patient based on said serial number.

20. A method for determining if an implantable medical device is magnetic resonance conditional comprising:
setting a default conservative magnetic resonance condition status in a memory of a first implantable medical device implanted in a patient,
wherein said implantable medical device comprises an implant transceiver,
wherein said memory comprises memory locations for flags that correspond to memory vales, and
wherein setting a default conservative MR condition status comprises setting the flags with the default conservative MR condition status;
accepting information in an external device at an implantation time related to magnetic resonance condition status of at least one second implantable medical device implanted in said patient,
wherein said external device is wirelessly communicatively coupled with said first implantable medical device,
wherein said external device comprises
an external transceiver that wirelessly communicates with said implant transceiver,
a data communication interface, and
a programmer with a programmer screen: and,
wherein said information is accepted as entered via said programmer;
determining if said information related to magnetic resonance conditional status is consistent with status of said at least one second implantable medical device implanted in said patient via said programmer;

applying a change in status in said memory of said first implantable device if said information related to magnetic resonance condition status is consistent with said status of said at least one second implantable medical device and storing a date, a time, or a combination thereof in said memory associated with said applying said change via said external device wirelessly communicatively coupled with said first implantable medical device;

transferring said information related to magnetic resonance condition status to a home monitoring service center during a home monitoring data upload via said data communication interface, wherein said home monitoring service center is communicatively coupled with said external device via said data communication interface, and wherein said home monitoring service center comprises a user interface;

accepting a request for said information related to magnetic resonance condition status of said at least one second implantable medical device at said home monitoring service center via said user interface;

displaying said information related to magnetic resonance condition status via said user interface;

obtaining a serial number associated with said first implantable medical device;

transferring said serial number to said home monitoring service center; and, obtaining an identity of said patient based on said serial number.

* * * * *